United States Patent
Ribeiro

(10) Patent No.: US 10,278,969 B2
(45) Date of Patent: May 7, 2019

(54) PHARMACEUTICAL DOSAGE FORMS

(71) Applicant: Novartis AG, Basel (CH)

(72) Inventor: Suzie Ribeiro, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/102,378

(22) PCT Filed: Dec. 11, 2014

(86) PCT No.: PCT/IB2014/066820
§ 371 (c)(1),
(2) Date: Jun. 7, 2016

(87) PCT Pub. No.: WO2015/087283
PCT Pub. Date: Jun. 18, 2015

(65) Prior Publication Data
US 2017/0007602 A1    Jan. 12, 2017

Related U.S. Application Data

(60) Provisional application No. 61/915,606, filed on Dec. 13, 2013.

(51) Int. Cl.
*A61K 31/506* (2006.01)
*A61K 9/16* (2006.01)
*A61K 9/48* (2006.01)
*A61K 9/00* (2006.01)

(52) U.S. Cl.
CPC .......... *A61K 31/506* (2013.01); *A61K 9/0053* (2013.01); *A61K 9/1635* (2013.01); *A61K 9/1652* (2013.01); *A61K 9/1682* (2013.01); *A61K 9/48* (2013.01); *A61K 9/4833* (2013.01); *A61K 9/4858* (2013.01); *A61K 9/4866* (2013.01)

(58) Field of Classification Search
CPC ...... A61K 31/506; A61K 9/4858; A61K 9/48; A61K 9/0053; A61K 9/1635; A61K 9/4833; A61K 9/1682; A61K 9/1652; A61K 9/4866
See application file for complete search history.

(56) References Cited

U.S. PATENT DOCUMENTS

2013/0165484 A1 *   6/2013  Radhakrishnan .... A61K 9/4858
                                                        514/345

FOREIGN PATENT DOCUMENTS

| WO | WO2006/000420 A1 | 1/2006 |
| WO | 2007071752 | 6/2007 |
| WO | WO2011/071821 A1 | 6/2011 |

* cited by examiner

*Primary Examiner* — Sudhakar Katakam
(74) *Attorney, Agent, or Firm* — Goodwin Procter LLP

(57) ABSTRACT

The present invention relates to solid pharmaceutical dosage forms comprising the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof. It further relates to processes of making said solid pharmaceutical dosage forms.

4 Claims, No Drawings

PHARMACEUTICAL DOSAGE FORMS

CROSS-REFERENCE TO RELATED APPLICATIONS

This application is a U.S. national stage application under 35 U.S.C. § 371 of International Application No. PCT/IB2014/066820, filed on Dec. 11, 2014, which application claims priority to and the benefit of U.S. Provisional Patent Application No. 61/915,606, filed on Dec. 13, 2013.

FIELD OF THE INVENTION

The present invention relates to solid pharmaceutical dosage forms comprising the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof. It further relates to processes of making said solid pharmaceutical dosage forms.

BACKGROUND OF THE INVENTION 3-(2,6-Dichloro-3,5-dimethoxy-phenyl)-1-{6-[4-(4-ethyl-piperazin-1-yl)-phenylamino]-pyrimidin-4-yl}-1-methyl-urea (described in U.S. Ser. No. 11/570,983, filed Jun. 23, 2005, and incorporated by reference in its entirety herein) has the structure of Formula I:

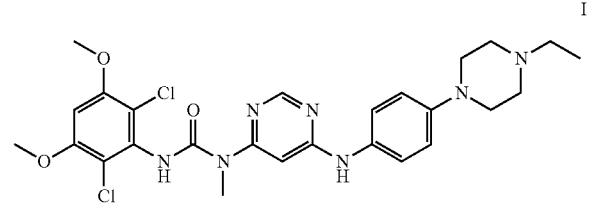 [SMILES: CCN1CCN(c2ccc(Nc3cc(N(C)C(=O)Nc4c(Cl)c(OC)cc(OC)c4Cl)ncn3)cc2)CC1]

I

The compound of Formula I (referred as the Compound hereafter) is a protein kinase inhibitor and is useful in the treatment of proliferative diseases mediated by protein kinases. In particular, the Compound inhibits FGFR1, FGFR2, FGFR3, FGFR4.

Several crystalline and amorphous forms of the Compound and methods to preparing said forms were described in WO 2011/071821 and are incorporated by reference in its entirety herein.

SUMMARY OF THE INVENTION

As every API has its own physical, chemical and pharmacological characteristics, a suitable pharmaceutical composition and dosage form has to be individually designed for every new API.

The design of a pharmaceutical composition, a pharmaceutical dosage form as well as a commercially viable pharmaceutical manufacturing process for the Compound is especially difficult for (inter alia) the following reasons:

The crystals of Compound in its free form as well as in some of its salt forms have a needle like shape and form a very voluminous and fluffy powder which is poorly flowable and difficult to process on pharmaceutical manufacturing machines.

Furthermore the urea bond of the Compound is prone to hydrolysis leading to the cleavage of the Compound into an "aniline degradant" and an "aminopyrimidine degradant".

Consequently, any residual water present in the drug itself or in the excipients making up the pharmaceutical composition or any aqueous media used in the manufacture of the drug product might cause the chemical degradation of the Compound.

It is therefore difficult to design a pharmaceutical composition or a dosage form for the Compound that is stable and is of an acceptable size to be easily swallowable. It is moreover difficult to design a manufacturing process which can be reliably produced at commercial scale.

In view of the above mentioned difficulties, the inventors tried to compact the voluminous Compound together with excipients without the use of aqueous media. However, the resulting drug material revealed high level of degradation product. There could be various root causes for the degradation problem. The inventor had run numerous experimental trials to identify the cause. It was surprisingly found that the application of mechanical stress during dry compaction process steps (e.g. roller compaction) resulted in the generation of the hydrolysis degradation products, thus resulted in stability issues. In contrast, counter-intuitive trials of the inventor to densify the compound together with binders and disintegrants by wet granulation to avoid mechanical stress turned out to significantly improve the stability profile despite of the fact that aqueous media were used as granulating fluids.

Taking these surprising findings into account, i.e. compaction/compression involving mechanical stress should be avoided, wet granulation with aqueous media, binders and disintegrants allows densification without causing stability issues, the inventors herewith provide the present invention in its following aspects.

In accordance with a first aspect of the present invention, there is provided a capsule for oral administration comprising
 (a) the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof,
 (b) one or more binders, and
 (c) one or more disintegrants.

In accordance with a second aspect of the invention, there is provided a pharmaceutical blend comprising
 (a) the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof,
 (b) one or more binders, and
 (c) one or more disintegrants,
wherein said blend has a bulk density of at least 0.4 g/mL. Preferably said blend is manufactured by a compression- and compaction-free process.

In accordance with a third aspect, there is provided a compression- and compaction-free process for making the capsules as defined by the first aspect comprising a wet granulation process step.

In accordance with a fourth aspect, there is provided a capsule obtainable by the compression- and compaction-free process according to the third aspect.

In accordance with a fifth aspect, there is provided a compression- and compaction-free process for making the pharmaceutical blend as defined by the second aspect and for making a capsule by machine-encapsulation of said pharmaceutical blend comprising a wet granulation process step.

In accordance with a sixth aspect, there is provided a pharmaceutical blend obtainable by the compression- and compaction-free process according to the fifth aspect and a capsule obtainable by said compression- and compaction-free process further comprises an additional encapsulation step.

The above mentioned aspects provide the following advantages:

By the densification of the voluminous drug substance and the excipients by wet granulation (1) the blend in an amount corresponding to a dose up to 125 mg of the Compound can be filled into a capsule of size 0 or smaller; and (2) it becomes feasible to fill the blend into capsules by machine; and (3) the drug becomes more easily swallowable by patients. By the avoidance of mechanical stress the formation of degradation products of the drug substance is minimized.

DETAILED DESCRIPTION OF THE INVENTION

Herein after, the present invention is described in further detail and is exemplified.

In the aspects of the present invention the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea, herein also referred to as the Compound, is present in its free form or in the form of any pharmaceutically acceptable salt salt, complex, co-crystal, hydrate or solvate thereof.

In one embodiment the Compound is present in its free base form.

In another embodiment the Compound is present as phosphate salt; in yet another embodiment as mono-phosphate salt; in yet another embodiment as anhydrous mono-phosphate salt.

In one embodiment, the Compound is present as anhydrous mono-phosphate salt in a polymorphic form characterized by an XRPD (X-ray powder diffraction) pattern comprising a characteristic peak (2theta) at about 15° or 15.0°±0.2°; further comprising one or more characteristic peaks (2theta) selected from peaks at about 13.7°, about 16.8°, about 21.3° and about 22.4°; even further comprising one or more characteristic peaks (2theta) selected from peaks at about 9.2°, about 9.6°, about 18.7°, about 20.0°, about 22.9° and about 27.2 as described in WO 2011/071821 A1 as "Form A". The latter disclosure provides the process for preparing this form (Example 3) and further details on the characterization of this form (Example 5 B) and is incorporated herein as reference.

In the aspects of the present invention the drug substance, i.e. the Compound, is present in the pharmaceutical blend or in the content of the capsule in an amount of at least 3%, preferably 3-80%, 3-70%, 3-60%, 3-50%, or 3-40%, preferably 3.0-40%, 3.5-40%, or 3.8-40%, preferably 6 to 70%, 8 to 70%, 10 to 70%, 15 to 70%, 20 to 70%, preferably 6 to 60%, 8 to 60%, 10 to 60%, 15 to 60%, 20 to 60%, preferably 3.9±1%, 9.7±2% or 31.6±5% by weight of the drug substance in its free base form based on the total weight of the blend or of the content of the capsule, respectively. The amount values above refer to the drug substance as free base, i.e. any possible salt-forming counter-ions are not included.

In the aspects of the present invention the binders include sugars (e.g. glucose, sucrose), gelatin, natural gums (e.g. acacia, tragacanth), sorbitol, maltodextrin, sodium alginate or alginate derivatives, polyvinylpyrrolidone (PVP, e.g. known under the brand name PVP K 30 PH by ISP Corp. and cellulose in various forms (e.g. microcrystalline cellulose) and derivatives (e.g. methylcellulose, ethylcellulose, hydroxypropylcellulose, hydroxypropylmethylcellulose).

Prefereably the binder is a cellulose derivative (e.g. methylcellulose, ethylcellulose, hydroxypropylcellulose, hydroxypropylmethylcellulose), more preferably a hydroxypropylmethylcellulose (HPMC), even more preferably Cellulose HP-M 603 (e.g. by DOW Chemical Corp).

The term "binder" is used herein in its established meaning in the field of pharmaceutics, e.g. as a promoter of cohesive compacts which enables to form granules and which ensures that granules can be formed with the required mechanical strength.

The inventors observed an increased initial in vitro drug release when the composition contains HPMC as binder compared to compositions not containing a binder. This indicates that HPMC, especially Cellulose HP-M 603, is a preferable binder for the present invention.

In the aspects of the present invention the binder(s) is (are) present in the pharmaceutical blend or in the content of the capsule in an amount of 0.1-70%, 0.5-70%, 0.5-60%, 0.5-50%, 0.5-40%, 0.5-30%, or 0.5-20% preferably 0.5-20% or 0.5-10%, more preferably 0.5-5% by weight based on the total weight of the blend or content of the capsule, respectively. The above mentioned ranges apply for all the binders as listed above.

Preferably, the binder is HPMC and is present in an amount of 0.5-10 or 0.5-5%, preferably in an amount of 1±0.5%, 2±1% or 3±1%.

In the aspects of the present invention disintegrants include-starch and its derivatives (e.g. low substistuted carboxymethyl starches such as Primogel® by Generichem Corp., Explotab® by Edward Mendell Co., or Tablo® by Blanver), pregelatinized starches, potato, maize, and corn starches), clays (e.g. Veegum HV and bentonite), cross-linked cellulose and its derivatives (e.g. cross-linked form of sodium carboxymethylcellulose (CMC), e.g. as known under the brand names AcDiSol® by FMC Corp., Nymcel ZSX by Nyma, Primellose® by Avebe, Solutab® by Blanver), cross-linked polyvinylpyrrolidone (PVP XL) e.g. as known under the brand names Crospovidone® by BASF Corp., Kollidon CUR) by BASF Corp., Polyplasdone XL® by ISP Chemicals LLC. Preferably, the disintegrant is a cross-linked polyvinylpyrrolidone. Preferably the particle size of said cross-linked PVP is characterized by 40-90% (m/m) of particle size sieve residue 63 µm, e.g. 68%, 5-80% (m/m) of particle size sieve residue 125 µm, e.g. 42%, 0-30% (m/m) of particle size sieve residue 250 µm, e.g. 15%.

The term "disintegrant" is used herein in its established meaning in the field of pharmaceutics, e.g. as a facilitator to break up granules or tablets into smaller fragments when getting in contact with liquids to promote rapid drug dissolution.

In a preferred embodiment of the invention, the disintegrant is crosslinked PVP (PVP XL). It was surprisingly observed that, in experiments when drug was extracted for analytical purposes, Compound A was extracted to the most completion in the formulation in which the disintegrant is PVP (PVP XL).

In the aspects of the present invention the disintegrant(s) is (are) present in the pharmaceutical blend or in the content of the capsule in an amount of 0.5-50%, 1-30%, 1-25%, 1-20%, 1-15%, or 1-12%, preferably 1-12%, more preferably 1-4% by weight based on the total weight of the blend or content of the capsule, respectively. The above mentioned ranges apply for all the disintegrants as listed above. Preferably, the disintegrant is crosslinked PVP (PVP XL) and is present in an amount of 1-30%, 1-25%, 1-20%, 1-15%, 1-12%, 1-10%, 1-5%, 1-4% or 1-3.5%, preferably 1-4%, more preferably of 2±1%, 2.5±1% or 3±1%, even more preferably about 2.3%, about 2.5% or about 3.3%.

All those percentage values are weight by weight percentage values and based on the total weight of the blend or content of the capsule.

According to the first aspect, the invention provides a capsule for oral administration comprising
(a) the drug substance 3-(2,6-dichloro-3,5-dimethoxyphenyl)-1-{6-[4-(4-ethyl-piperazin-1-yl)-phenylamino]-pyrimidin-4-yl}-1-methyl-urea or any pharmaceutically acceptable salt thereof,
(b) one or more binders, and
(c) one or more disintegrants.
Optionally, said capsule may further comprise
(d) one or more fillers, preferably selected from the group of microcrystalline cellulose, lactose and/or mannitol, preferably in an amount of 10-95% by weight based on the total weight of the content of the capsule,
(e) one or more lubricants, preferably magnesium stearate in an amount of 0.1-3%, preferably 0.2-2% by weight based on the total weight of the content of the capsule, and/or
(f) one or more glidants, preferably colloidal silicon dioxide (colloidal silica), preferably in an amount of 0.1-2%, preferably 0.1-0.5% by weight based on the total weight of the content of the capsule.

The capsule may be a hard capsule or a soft capsule, preferably made out of gelatin and optionally comprising colourants, process aids (e.g. sodium lauryl sulfate), and/or preservatives. Preferably, the capsule is a hard gelatin capsule.

The size of the capsule may range from 0 (body volume 0.69 mL), 1, 2, 3 or 4 (body volume 0.20 mL). Preferably, for the present invention a capsule of size 0 is used for a dosage strength of 125 mg, a capsule of size 1 is used for a dosage strength of 100 mg, a capsule of size 3 or 4 is used for a dosage strength of 25 mg. The sizes of the capsule herein refers to as the standardized sizes for two-pieces hard capsules in the pharmaceutical industry practice, e.g. capsule size "1" has a volume of about 0.5 mL, e.g. 0.48-0.50 mL, a locked length of about 19-20 mm e.g. 19.4 mm, and an external diameter of about 7 mm, e.g. 6.6 or 6.9 mm.

It is one of the advantages of the present invention, that a relatively small capsule sizes can be used, which is based on the densified pharmaceutical blend as described in further detail below, which allows to deliver the required high doses (e.g. up to 125 mg per unit) of the drug substance via easily swallowable dosage forms.

According to the second aspect, the invention provides a pharmaceutical blend comprising
(a) the drug substance 3-(2,6-dichloro-3,5-dimethoxyphenyl)-1-{6-[4-(4-ethyl-piperazin-1-yl)-phenylamino]-pyrimidin-4-yl}-1-methyl-urea or any pharmaceutically acceptable salt thereof,
(b) one or more binders, and
(c) one or more disintegrants.
wherein said blend has a bulk density of at least 0.4 g/mL, preferably at least 0.5 g/mL, at least 0.6 g/mL, or 0.7 g/mL. Preferably said pharmaceutical blend is manufactured by a compression- and compaction-free process, preferably a process comprising wet granulation.

Optionally, said pharmaceutical blend may further comprise
(d) one or more fillers, selected from the group of microcrystalline cellulose, lactose and/or mannitol, preferably in an amount of 10-95% by weight based on the total weight of the content of the capsule, and/or
(e) one or more lubricants, preferably magnesium stearate, preferably in an amount of 0.1-3%, preferably, 0.2-2% by weight based on the total weight of the content of the capsule, and/or
(f) one or more glidants, preferably colloidal silicon dioxide (colloidal silica), preferably in an amount of 0.1-2%, preferably, 0.1-0.5% by weight based on the total weight of the content of the capsule.

Due to the use of suitable binders and disintegrants the voluminous drug substance can be densified to such an extent that at least 250 mg of the pharmaceutical blend of the present invention can be filled into a capsule of size 1 with a body volume of 0.5 mL or a capsule of smaller size.

Therefore, the bulk density of the pharmaceutical blend of the present invention is the "poured bulk density" before capsule filling and is at least 0.4 g/mL, 0.5 g/mL, 0.6 g/mL, 0.7 g/mL, 0.8 g/mL 0.9 g/mL, 1.0 g/mL, 1.1 g/mL or 1.2 g/mL, Alternatively, the bulk density of the pharmaceutical blend of the present invention is the "poured bulk density" after capsule filling and is at least 0.4 g/mL, 0.5 g/mL, 0.6 g/mL, 0.7 g/mL, 0.8 g/mL 0.9 g/mL, 1.0 g/mL, 1.1 g/mL or 1.2 g/mL, preferably at least 0.4 g/mL. Alternatively, the bulk density of the pharmaceutical blend of the present invention is the "tapped bulk density" and is at least 0.5 g/mL, 0.6 g/mL, 0.7 g/mL, 0.8 g/mL 0.9 g/mL, 1.0 g/mL, 1.1 g/mL or 1.2 g/mL, preferably at least 0.5 g/mL, at least 0.6 g/mL, or at least 0.7 g/mL.

Preferably, the bulk density of the pharmaceutical blend of the present invention is the "tapped bulk density" and is at least 0.5 g/mL, 0.6 g/mL, 0.7 g/mL, 0.8 g/mL 0.9 g/mL, 1.0 g/mL, 1.1 g/mL or 1.2 g/mL, preferably at least 0.5 g/mL, at least 0.6 g/mL, or at least 0.7 g/mL, more preferably at least 0.6 g/mL.

The "poured bulk density" is often also referred to as "freely settled density" or "initial bulk density" or "fluff bulk density", i.e. the density the powder posseses as a result from merely pouring it into a receiving container. The "tapped bulk density" is often also referred to as "consolidated bulk density", measured according to the standard methods as defined in Pharmacopeia, e.g. the European Pharmacopeia, using standardized equipment (e.g. 250 ml graduated cylinder (readable to 2 ml) with a mass of 220±44 g; and a settling apparatus capable of producing, in 1 minute, either nominally 250±15 taps from a height of 3±0.2 mm, or nominally 300±15 taps from a height of 14±2 mm. The support for the graduated cylinder, with its holder, has a mass of 450±10 g. According to said standard methods 500 and 1250 taps on the same powder sample (100 g) is carried out and the corresponding volumes V500 and V1250 are determined. If the difference between V500 and V1250 is less than or equal to 2 mL, V1250 is the tapped volume. If the difference between V500 and V1250 exceeds 2 ml, one has to repeat in increments such as 1250 taps, until the difference between succeeding measurements is less than or equal to 2 ml. The tapped bulk density is then the 100 g sample weight divided by the (final) V1250 volume.

As the inventors have surprisingly found that the application of mechanical stress (e.g. during an roller compaction step) causes the generation of degradation products known from hydrolysis reactions of the drug substance, it is important for the present invention to design a manufacturing process which avoids substantial mechanical stress by any compression and/or compaction process step. A substantially compression-free and compaction-free process according to the present invention is a process by which the components of the blend during manufacturing of the blend and the final blend itself are subjected to mechanical forces not in the kilo Newton (kN) range, preferably not exceeding 10 kN, preferably not exceeding 4 kN, more preferably not exceeding 1 kN. In one embodiment such a substantially compression-free and compaction-free process comprises a step of wet granulation. The low levels of mechanical stress potentially caused by high shear mixers, screening mills or by kneading typically involved in wet granulation are according to the present invention deemed negligible. Also deemed negligible are the low compaction forces (typically 10-100 N) which are applied during a capsule filling process to softly compact a blend powder to form a so-called "plug" of powder or "plugs". Examples for the presence of substantial mechanical stress are in roller compaction steps (typical specific compaction forces of about 4-80 kN/cm, more typically 10-64 kN/cm of roller length) and tablet compression steps (typical compression forces from about 5 kN up to 100 kN or higher).

Accordingly, in the third aspect the present invention provides a compression- and compaction-free process for making the capsules as defined by the first aspect of the invention comprising a wet granulation process step, preferably a wet granulation which is performed by using an aqueous granulating fluid, preferably water.

More specifically, the compression- and compaction-free process according to the third aspect is characterized by the following process steps:

(1) wet granulating the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof, with one or more binders, and one or more disintegrants, and an aqueous granulating fluid, preferably water, and optionally one or more additional pharmaceutical excipients, to obtain granules, (2) mixing the granules of step 1 with additional pharmaceutical excipients, e.g. glidants (preferably colloida silica or silicium dioxide) and lubricants (preferably magnesium stearate) and optionally further fillers (preferably mannitol or lactose) or disintegrants (preferably PVP XL) to obtain a pharmaceutical blend.

(3) machine-encapsulation of the pharmaceutical blend of step 2 into capsules, preferably hard gelatin capsules.

In a fourth aspect, the capsules resulting from said process are provided.

The term "machine-encapsulation" is used herein to contrast the process of the present invention from any process in which the capsules are filled by hand or with the help of simple pieces of equipment (e.g. plastic plates with pre-drilled holes) and simple loading devices. With such bench-scale fillings only small quantities of capsules can be produced, typically up from 50 to 5,000 capsule per hour. Instead, "machine-encapsulation" herein refers to industrial-scale filling by machines like the auger filling machine using a ring system or the Zanasi as dosing tube or dosator-type machine or the Höfliger & Karg as dosing disc and tamping finger machine. With such semi-automatic to full-automatic machines capsules can be produced with outputs of typically 5000-150,000 capsules per hour (caps/h).

In accordance with a fifth aspect, there is provided a compression- and compaction-free process for making the pharmaceutical blend as defined by the second aspect and for making a capsule by machine-encapsulation of said pharmaceutical blend comprising a wet granulation process step, said wet granulation step is preferably performed by using an aqueous granulating fluid, preferably water.

More specifically, the compression- and compaction-free process according to the fifth aspect is characterized by the following process steps:

(1) wet granulating the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea or any pharmaceutically acceptable salt thereof with one or more binders, and one or more disintegrants, and an aqueous granulating fluid, preferably water, and optionally one or more additional pharmaceutical excipients to obtain granules, (2) mixing the granules of step 1 with additional pharmaceutical excipients to obtain a pharmaceutical blend.

In addition, it is provided a compression- and compaction-free process for making a capsule comprising the steps 1 and 2 according to the fifth aspect as described above and further comprising the step of (3) machine-encapsulation of the pharmaceutical blend of step 2 into capsules, preferably hard gelatin capsules.

As a sixth aspect, there is provided a pharmaceutical blend obtainable by the compression- and compaction-free process according to fifth aspect.

As a modification of the sixth aspect, there is provided a capsule obtainable by the compression- and compaction-free process according to the fifth aspect including the machine-encapsulation step 3.

As a further aspect, there is provided a dose unit comprising the capsule of the first aspect or the pharmaceutical blend according to the second aspect in the form of a capsule. More specifically, the dose unit according to this further aspect comprises the drug substance, i.e. the Compound in its free base form in an amount of 1-150 mg, preferably 10-125 mg, more preferably 10 mg, 25 mg, 100 mg or 125 mg.

As a further aspect, there is provided a capsule according to the first aspect wherein the size of the capsule is 0 and comprises up to 100 mg, or up to 125, or up to 150 mg, preferably up to 125 mg, more preferably 100 mg to 150 mg of drug, even more preferably 100 mg or 125 mg, even more preferably 125 mg of the Compound or any of its pharmaceutical acceptable salt, wherein the drug dose is calculated in its free base form of the compound.

As a further aspect, there is provided a capsule according to the first aspect wherein the size of the capsule is 1 and comprises up to 100 mg, or up to 125, or up to 150 mg, preferably up to 100 mg, more preferably 50 mg to 100 mg, even more preferably 100 mg of the Compound or any of its pharmaceutical acceptable salt, wherein the drug dose is calculated in its free base form of the compound.

As a further aspect, there is provided a capsule according to the first aspect wherein the size of the capsule is 2 and comprises up to 50 mg, or up to 75, or up to 100 mg, preferably up to 50 mg, more preferably 25 mg to 50 mg, even more preferably 50 mg of the Compound or any of its pharmaceutical acceptable salt, wherein the drug dose is calculated in its free base form of the compound.

As a further aspect there is provided a capsule according to the first aspect wherein the size of the capsule is 3 or 4 and comprises up to 10 mg, or up to 25, or up to 50 mg, preferably up to 25 mg, preferably 25 mg, of the Compound or any of its pharmaceutical acceptable salt, wherein the drug dose is calculated in its free base form of the compound.

The following are preferred embodiments of the present invention:

A capsule for oral administration comprising:
(a) 3-40% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose, and
(c) 1-4% by weight of crosslinked polyvinylpyrrolidone,
based on the total weight of the content of the capsule.

A capsule for oral administration comprising:
(a) 3-40% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose,
(c) 1-4% by weight of crosslinked polyvinylpyrrolidone, and optionally further comprising,
(d) 10-95% by weight of cellulose, lactose and/or mannitol
based on the total weight of the content of the capsule.

In a preferred embodiment, the range of the drug substance is 26.6-36.6%.

In a preferred embodiment, the range of hydroxypropylmethylcellulose is 2-4%.

In a preferred embodiment, the range of crosslinked polyvinylpyrrolidone is 2-4%.

In a very preferred embodiment, the present invention provides

A capsule for oral administration comprising:
(a) 26.6-36.6% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 2-4% by weight of hydroxypropylmethylcellulose,
(c) 2-4% by weight of crosslinked polyvinylpyrrolidone, and optionally further comprising,
(d) 10-95% by weight of cellulose, lactose and/or mannitol
based on the total weight of the content of the capsule.

A capsule for oral administration comprising:
(a) 3-40% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose,
(c) 1-4% by weight of crosslinked polyvinylpyrrolidone, and optionally further comprising,
(d) 10-95% by weight of cellulose, lactose and/or mannitol,
(e) 0.2-2% by weight of magnesium stearate, and
(f) 0.1-0.5% by weight of colloidal silica,
based on the total weight of the content of the capsule.

A capsule for oral administration comprising, consisting essentially of or consisting of:
(a) 3-15% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose,
(c) 1-4% by weight of crosslinked polyvinylpyrrolidone,
(d) 75-95% by weight of cellulose, lactose and/or mannitol,
(e) 0.2-2% by weight of magnesium stearate, and
(f) 0.1-0.5% by weight of colloidal silica,
based on the total weight of the content of the capsule.

A capsule for oral administration comprising, consisting essentially of or consisting of:
(a) 30-45% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose,
(c) 1-4% by weight of crosslinked polyvinylpyrrolidone,
(d) 35-65% by weight of cellulose, lactose and/or mannitol,
(e) 0.2-2% by weight of magnesium stearate, and
(f) 0.1-0.5% by weight of colloidal silica,
based on the total weight of the content of the capsule.

A capsule for oral administration comprising, consisting essentially of or consisting of:
(a) 30-45% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
(b) 0.5-5% by weight of hydroxypropylmethylcellulose,
(c) 1-4% by weight of crosslinked polyvinylpyrrolidone,
(d) 45-65% by weight of cellulose, lactose and/or mannitol,
(e) 0.2-2% by weight of magnesium stearate, and
(f) 0.1-0.5% by weight of colloidal silica,
based on the total weight of the content of the capsule.

EXAMPLES

Hereinafter, the present invention is described in more details and specifically with reference to the examples, which however are not intended to limit the present invention.

Example 1: Manufacturing Process for 10, 25, and 100 mg Dosage Strength

In the following, the manufacturing process is outlined for all exemplified dosage strength. The corresponding amounts of the ingredients are provided in the formulas under Examples 1.1, 1.2 and 1.3 below.

Manufacturing of the Blend:

Compound present as monophosphate, cellulose MK-GR, lactose milled, PVP XL and cellulose HPM603 are pre-mixed in a wet high-shear vertical granulator to obtain a dry blend. Purified water is incrementally added as granulation liquid to an amount adding up to about 35-37% of the inner phase with an addition rate of up to 600 g/min.

The resulting granulation mixture is kneaded for about 3-4 min.

Suitable equipment used for those process steps are e.g. Aeromatic Fielder GP150/Fiedler 65L (impeller setting of 60-270 rpm, preferably 150 rpm and chopper settings of 600-3000 rpm, preferably 1500 rpm), or Colette Gral 75L (impeller setting of 203-306 rpm, preferably 300 rpm and chopper settings of 1500-3000 rpm) or equivalent.

The kneaded granulation mass is screened through a 3.0 mm in a oscillator or rotating screening mill, e.g. Alexander RAN 70, Frewitt or equivalent, with 90-600 rpm. This process step is optional and may be omitted, preferably this process step is performed.

The granules are dried in a fluidized bed dryer, e.g. Aeromatic Fiedler MP1, TR02 or Glatt FBD or equivalent, with in inlet air temperature of 55-65° C., preferably 60° C., a product temperature of 30-40° C. and an inlet air volume of 300-1200 m³/h. The drying endpoint indicated by a loss-of-drying (LOD) readout of 2.2% is achieved after about 30-45 min. Alternatively, the granules are dried in a Fiedler TK65 vessel with a jacket temperature of 45-65° C., a cover temperature of 48-68° C., at an impeller speed of about 60 rpm with a vacuum of 30-50 mbar to reach within 7 hours or less a drying endpoint of 2.2%.

The dried granules are screened through 1.0 mm or alternatively 1016 µm in a screening mill with an oscillating bar or rotating impeller (e.g. Alexander RAN 70, Frewitt or equivalent) with ca. 47-177 rpm within about 3 min. The resulting dried and screened granules are also referred to herein as inner phase.

The outer phase excipients PVP XL, Mannitol (only for 10 and 25 mg dosage strength), and Aerosil 200 are screened through 1.0 mm or alternatively 1016 µm in a screening mill with an oscillating bar or rotating impeller (e.g. Alexander RAN 70, Frewitt or equivalent) with ca. 47-177 rpm and then combined with the inner phase in an suitable container.

Said solids are lubricated by addition of magnesium stearate as an additional outer phase excipient by blending in a diffusion mixer (tumble) or bin blender (e.g. Bohle PM400, Turbula or equivalent) for about 5 min at 4-25 rpm, preferably 15 rpm, to obtain the final blend which is ready for capsule filling.

Manufacturing of the Capsules:

The final blend is then filled into capsules of size 1 by encapsulation machines with dosing plate principle or with dosing tube (e.g. Höfliger & Karg GKF 330, Bosch GKF 1500, Zanasi 12 E, Zanasi 40 E) with encapsulation speeds of 10,000 up to 100,000 caps/h. The weights of the capsules are controlled and the capsules dedusted.

Example 1.1: Formula for 10 mg Dosage Strength

| Component | Composition per unit [%] | Composition per unit [mg/unit] | Quantity per 100'000 units [kg/batch] |
|---|---|---|---|
| Compound as monophosphate[a] | 4.54[a] | 11.75[a] | 1.175[a] |
| Cellulose MK-GR | 8.49 | 22.00 | 2.200 |
| Lactose milled | 9.85 | 25.50 | 2.550 |
| Cellulose HPM603 | 0.77 | 2.00 | 0.200 |
| Polyvinylpolypyrrolidon XL | 0.77 | 2.00 | 0.200 |
| Purified water[b] | | | |
| Total inner phase | | 63.25 mg | 6.325 kg |
| Polyvinylpolypyrrolidon XL | 1.57 | 4.070 | 0.407 |
| Mannitol DC | 72.22 | 187.05 | 18.705 |
| Aerosil 200 | 0.30 | 0.78 | 0.078 |
| Magnesium stearate | 1.49 | 3.850 | 0.385 |
| Total final blend | 100.0% | 259.0 mg | 25.90 kg |
| Hard gelatin capsule, size 1 | | 76.0 mg | |
| Total capsule weight | | 335.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 1.2: Formula for 25 mg Dosage Strength

| Component | Composition per unit [%] | Composition per unit [mg/unit] | Quantity per 100'000 units [kg/batch] |
|---|---|---|---|
| Compound as monophosphate[a] | 11.34[a] | 29.375[a] | 2.9375[a] |
| Cellulose MK-GR | 21.24 | 55.00 | 5.500 |
| Lactose milled | 24.61 | 63.75 | 6.375 |
| Cellulose HPM603 | 1.93 | 5.00 | 0.50 |
| Polyvinylpolypyrrolidon XL | 1.93 | 5.00 | 0.50 |
| Purified water[b] | | | |
| Total inner phase | | 158.125 mg | 158.125 kg |
| Polyvinylpolypyrrolidon XL | 0.56 | 1.46 | 0.146 |
| Mannitol DC | 36.60 | 94.785 | 9.478 |
| Aerosil 200 | 0.30 | 0.780 | 0.078 |
| Magnesium stearate | 1.49 | 3.85 | 0.385 |
| Total final blend | 100.0% | 259.0 mg | 25.90 kg |
| Hard gelatin capsule, size 1 | | 76.0 mg | |
| Total capsule weight | | 335.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 1.3: Formula for 100 mg Dosage Strength

| Component | Composition per unit [%] | Composition per unit [mg/unit] | Quantity per 100'000 units [kg/batch] |
|---|---|---|---|
| Compound as monophosphate[a] | 37.18[a] | 117.5[a] | 11.75[a] |
| Cellulose MK-GR | 25.63 | 81.0 | 8.10 |
| Lactose milled | 29.43 | 93.0 | 9.30 |
| Cellulose HPM603 | 3.164 | 10.0 | 1.0 |
| Polyvinylpolypyrrolidon XL | 3.164 | 10.0 | 1.0 |
| Purified water[b] | | | |
| Total inner phase | | 311.5 mg | 31.15 kg |
| Polyvinylpolypyrrolidon XL | 0.101 | 0.32 | 0.032 |
| (Mannitol DC) | (n.a.) | (n.a.) | (n.a.) |
| Aerosil 200 | 0.130 | 0.41 | 0.041 |
| Magnesium stearate | 1.201 | 3.80 | 0.380 |
| Total final blend | 100.0% | 316.03 mg | 316.03 kg |
| Hard gelatin capsule, size 1 | | 76.0 mg | |
| Total capsule weight | | 392.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 2: Manufacturing Process for 25, 100, and 125 mg Dosage Strength

In the following, the manufacturing process is outlined for all exemplified dosage strength.

The corresponding amounts of the ingredients are provided in the formulas under Examples 2.1, 2.2 and 2.3 below.

Manufacturing of the Blend:

Cellulose MK-GR, lactose (milled), the Compound, cellulose HPM 603 and cross-linked polyvinylpyrrolidone (PVP-XL) are sequentially added into a vertical wet high-shear granulator (e.g. TK Fiedler (bottom driven, 65 L) with a granulator fill volume of about 45-50%, the five components are then mixed at 60-270 rpm, preferably 150 rpm (impeller setting) and 600-3000, preferably 1500 rpm (chopper setting) for about 5 min to obtain a dry blend.

Purified water is added as granulation liquid at rate of about 385 g/min for 7 min (adding up to about 2.7 kg water) with a spray setting pressure of 1.5 bar (impeller setting of 60-270 rpm, preferably 150 rpm and chopper settings of 600-3000 rpm, preferably 1500 rpm). The resulting granulation mixture is kneaded for about 3 min (impeller setting of 60-270 rpm, preferably 150 rpm and chopper settings of 600-3000 rpm, preferably 1500 rpm). The kneaded granulation mass is screened through a 3.0 mm sieve using a Comil with 90-600 rpm. This process step is optional and may be omitted, preferably this process step is performed.

The granules are dried in a fluidized bed dryer, e.g. Glatt GPCG 15/30 or equivalent, with an inlet air temperature of 55-65° C., preferably 60° C., a product temperature of about 30-40° C. and an inlet air volume of 300-1200 m$^3$/h to reach a drying endpoint of ≤2.2%.

The dried granules are screened through 800-1000 μm in a Comil. The resulting dried and screened granules are also referred to herein as inner phase.

The outer phase excipients PVP XL and Aerosil 200 are screened through 900-1000 μm in a Comil with ca. 50-150 rpm and then combined with the inner phase in a suitable container (e.g. bin blender, turbula or equivalent) by mixing with 4-25 rpm, preferably 17 rpm for about 5 min (33-66% powder fill).

Said solids are lubricated by addition of 500 rpm-screened magnesium stearate as an additional outer phase excipient by blending in a diffusion mixer (tumble) or bin blender (e.g. Bohle PM400, Turbula or equivalent) for about 3 min at about 17 rpm, to obtain the final blend which is ready for capsule filling.

Manufacturing of the Capsules:

The final blend is then filled into hard gelatin capsules (HGC) of size 0, 1, or 3 by encapsulation machines with dosing plate principle or with dosing tube (e.g. Höfliger & Karg GKF 330, Bosch GKF 1500, Zanasi 12 E, Zanasi 40 E) with encapsulation speeds of 10,000 up to 100,000 caps/h and without precompression. The weights of the capsules are controlled and the capsules dedusted.

Example 2.1: Formula for 25 mg Dosage Strength

| Component | Composition per unit [%] | Composition per unit [mg/unit] | Quantity per 173'016 units [kg/batch] |
|---|---|---|---|
| Compound as monophosphate[a] | 37.18[a] | 29.38[a] | 5.084[a] |
| Cellulose MK-GR | 25.63 | 20.25 | 3.505 |
| Lactose milled | 29.43 | 23.25 | 4.024 |
| Cellulose HPM603 | 3.16 | 2.50 | 0.433 |
| Polyvinylpolypyrrolidon XL | 3.16 | 2.50 | 0.433 |
| Purified water[b] | | | |
| Total inner phase | | 77.88 mg | 13.48 kg |
| Polyvinylpolypyrrolidon XL | 0.10 | 0.08 | 0.0138 |
| Aerosil 200 | 0.13 | 0.10 | 0.0177 |
| Magnesium stearate | 1.20 | 0.95 | 0.164 |
| Total final blend | 100.0% | 79.01 mg | 13.67 kg |
| Hard gelatin capsule, size 3 | | 48.00 mg | |
| Total capsule weight | | 127.01 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 2.2: Formula for 100 mg Dosage Strength

| Component | Composition per unit [%] | Composition per unit [mg/unit] | Quantity per 43'255 units [kg/batch] |
|---|---|---|---|
| Compound as monophosphate[a] | 37.18[a] | 117.5[a] | 5.084[a] |
| Cellulose MK-GR | 25.63 | 81.0 | 3.505 |
| Lactose milled | 29.43 | 93.0 | 4.024 |
| Cellulose HPM603 | 3.16 | 10.0 | 0.433 |
| Polyvinylpolypyrrolidon XL | 3.16 | 10.0 | 0.433 |
| Purified water[b] | | | |
| Total inner phase | | 311.5 mg | 13.48 kg |
| Polyvinylpolypyrrolidon XL | 0.10 | 0.32 | 0.0138 |
| Aerosil 200 | 0.13 | 0.41 | 0.0177 |
| Magnesium stearate | 1.20 | 3.80 | 0.164 |
| Total final blend | 100.0% | 316.03 mg | 13.67 kg |
| Hard gelatin capsule, size 1 | | 76.00 mg | |
| Total capsule weight | | 392.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 2.3: Formula for 125 mg Dosage Strength

| Component | Composition per unit [%] | Composition per unit [mg/unit] | Quantity per 34'605 units [kg/batch] |
|---|---|---|---|
| Compound as monophosphate[a] | 37.18[a] | 146.875[a] | 5.084[a] |
| Cellulose MK-GR | 25.63 | 101.25 | 3.505 |
| Lactose milled | 29.43 | 116.25 | 4.024 |
| Cellulose HPM603 | 3.16 | 12.5 | 0.433 |
| Polyvinylpolypyrrolidon XL | 3.16 | 12.5 | 0.433 |
| Purified water[b] | | | |
| Total inner phase | | 389.4 mg | 13.48 kg |
| Polyvinylpolypyrrolidon XL | 0.10 | 0.40 | 0.0138 |

-continued

| Component | Composition per unit [%] | Composition per unit [mg/unit] | Quantity per 34'605 units [kg/batch] |
|---|---|---|---|
| Aerosil 200 | 0.13 | 0.513 | 0.0177 |
| Magnesium stearate | 1.20 | 4.75 | 0.164 |
| Total final blend | 100.0% | 395.03 mg | 13.67 kg |
| Hard gelatin capsule, size 0 | | 96.00 mg | |
| Total capsule weight | | 491.0 mg | |

[a] The salt factor is 1.175. The drug substance quantity has to be adjusted if the content is ≤99.5%. Respective compensation is done by adjusting lactose content.
[b] The water used during granulation is removed in the process of drying.

Example 3: Density and Flow Properties of Blends

Capsules were prepared according to the process as described in example 1 but at small scale (less than 0.5 kg) and using a 1.7 L Mi-Pro bottom-driven granulator, aeromatic fluid bed dryer (1.0 L Strea) and manual capsule filling equipment Bonapace.

Table 3 provides the amounts of the components as used as well as the results of the bulk and tapped density measurements (according to European Pharmacopoeia) and of the flowability analysis (Carr index, Hausner factor) of the final blends before capsule filling. Table 3 also provides the outcome of the capsule filling with respect to yield and rejection rate.

All blends showed a bulk density (poured density) of higher than 0.4 g/mL and a tapped density higher than 0.5 g/mL.

The 100 mg final blend showed good flow properties with low risk of cohesiveness as shown by Carr index and Hauser factor. However, the 10 mg and 25 mg blend was classified as "passable" showing a potential higher risk of flow problems.

For all dose strength acceptable capsule sorting yields above 95% were found. However, a higher yield and a lower number of rejects were observed for the 100 mg blend.

These findings demonstrate the superiority of the 100 mg blend over the 10 and 25 mg blends.

The 100 mg blend as described in this example 3 and the 100 mg blend of example 1, and all the blends of example 2 are therefore regarded as preferred embodiments of the invention.

The invention claimed is:

1. A capsule for oral administration that encapsulates a pharmaceutical blend comprising
    (a) 20-60% by weight of the drug substance 3-(2,6-dichloro-3,5-dimethoxy-phenyl)-1-{6-[4-(4-ethyl-piperazin-1-yl)-phenylamino]-pyrimidin-4-yl}-1-methyl-urea in its free base form, present as mono-phosphate salt,
    (b) 0.5-5% by weight of hydroxypropylmethylcellulose,
    (c) 1-4% by weight of crosslinked polyvinylpyrrolidone, and
    (d) a filler selected from the group consisting of a cellulose, lactose, mannitol, and combinations thereof;

TABLE 3

| Example | 3.1 | | 3.2 | | 3.3 | |
|---|---|---|---|---|---|---|
| Dose strength | 10 mg | | 25 mg | | 100 mg | |
| Component | mg | % | mg | % | mg | % |
| Internal phase (granules) | | | | | | |
| Compound as monophosphate | 11.75 | 3.89 | 29.38 | 9.73 | 117.50 | 36.72 |
| Cellulose MK-GR | 22.00 | 7.29 | 55.00 | 18.21 | 81.00 | 25.31 |
| Lactose milled | 25.50 | 8.45 | 63.75 | 21.11 | 93.00 | 29.06 |
| Cellulose HPM 603 | 2.00 | 0.66 | 5.00 | 1.66 | 10.00 | 3.13 |
| PVP-XL | 2.00 | 0.66 | 5.00 | 1.66 | 10.00 | 3.13 |
| External phase | | | | | | |
| PVP-XL | 4.70 | 1.56 | 1.70 | 0.56 | 0.50 | 0.16 |
| Mannitol DC | 228.60 | 75.71 | 136.78 | 45.29 | 2.35 | 0.73 |
| Aerosil 200 | 0.90 | 0.30 | 0.90 | 0.30 | 0.90 | 0.28 |
| Mg stearate | 4.50 | 1.49 | 4.50 | 1.49 | 4.75 | 1.48 |
| Total final blend | 302.0 | 100 | 302.0 | 100 | 320.0 | |
| HGC, size 1 | 76 | | 76 | | 76 | |
| Total cap weight | 378.0 | | 378.0 | | 396.0 | |
| Density of final blend | | | | | | |
| Bulk density (mL/100 g) | | | 216 | | 212 | |
| Bulk density (g/mL) | | | 0.463 | | 0.472 | |
| Tapped V500 (mL/100 g) | | | 174 | | 182 | |
| Tapped V1250 (mL/100 g) | | | 172 | | 180 | |
| Tapped density (g/mL) | | | 0.581 | | 0.556 | |
| Flowability | | | | | | |
| Carr Index | | | 20.37 good | | 15.10 very good | |
| Hausner factor | | | 1.26 passable | | 1.18 good | |
| Yield | | | | | | |
| Total no. of capsules | 1761 | | 1784 | | 1479 | |
| Sorting weight range (mg) | 356-400 | | 356-400 | | 372-420 | |
| Cap·s within sorting range (%) | 97.0 | | 96.7 | | 97.9 | |
| Total no. of rejects (%) | 3.0 | | 3.3 | | 2.1 | | wherein the weight percentages are based on the total weight of the pharmaceutical blend content of the capsule.

2. The capsule of claim 1, wherein the pharmaceutical blend has a poured bulk density of at least 0.4 g/mL.

3. The capsule of claim 1, wherein the pharmaceutical blend comprises 30-45% of the drug substance.

4. The capsule of claim 3, wherein the pharmaceutical blend comprises:
   2-4% by weight of hydroxypropylmethylcellulose, and
   2-4% by weight of crosslinked polyvinylpyrrolidone.

\* \* \* \* \*